United States Patent
Bieberich et al.

(10) Patent No.: US 7,100,394 B2
(45) Date of Patent: Sep. 5, 2006

(54) APPARATUS TO ADAPT A CONVECTIVE TREATMENT SYSTEM OR DEVICE FOR COOLING

(75) Inventors: Mark Thomas Bieberich, Minnetonka, MN (US); Ryan S. Augustine, Bloomington, MN (US); Scott D. Augustine, Bloomington, MN (US); Mark Christopher Albrecht, Chanhassen, MN (US)

(73) Assignee: Arizant HealthCare Inc., Eden Prairie, MN (US)

( * ) Notice: Subject to any disclaimer, the term of this patent is extended or adjusted under 35 U.S.C. 154(b) by 334 days.

(21) Appl. No.: 10/261,160

(22) Filed: Sep. 27, 2002

(65) Prior Publication Data

US 2004/0060318 A1 Apr. 1, 2004

(51) Int. Cl.
*F25D 3/02* (2006.01)

(52) U.S. Cl. .............................. 62/420; 62/421; 62/425; 62/460

(58) Field of Classification Search ........... 62/420–425, 62/406, 459, 460
See application file for complete search history.

(56) References Cited

U.S. PATENT DOCUMENTS

| | | | | |
|---|---|---|---|---|
| 3,498,076 A | * | 3/1970 | Michael | 62/244 |
| 3,777,506 A | * | 12/1973 | Hergatt et al. | 62/237 |
| 5,046,329 A | * | 9/1991 | Travis, III | 62/259.3 |
| 5,159,819 A | * | 11/1992 | Wong | 62/419 |
| 5,197,301 A | * | 3/1993 | Holcomb | 62/457.1 |
| 5,709,104 A | * | 1/1998 | Howcroft | 62/457.1 |
| 6,026,653 A | * | 2/2000 | Presnell | 62/177 |
| 6,170,282 B1 | * | 1/2001 | Eddins | 62/259.3 |
| 6,354,099 B1 | * | 3/2002 | Bieberich | 62/259.3 |
| 6,571,568 B1 | * | 6/2003 | Link | 62/244 |
| 6,571,574 B1 | | 6/2003 | Blackstone | |

OTHER PUBLICATIONS

Porta–Chill, The Portable Air–Chiller, Feb. 2002, pp. 1–9.
"Porta–Chill™ The Portable Air–Chiller", downloaded from the Internet, www.portachill.com. 3 pg.

* cited by examiner

*Primary Examiner*—Denise L. Esquivel
*Assistant Examiner*—Filip Zec
(74) *Attorney, Agent, or Firm*—Incaplaw; Terrance A. Meador

(57) ABSTRACT

An adaptor enables a convective treatment system to be modified for cooling by providing a bath of pressurized, cooled air intended to lower the body core temperature of a person. The adaptor may be constructed for being coupled between a blower assembly that provides a stream of pressurized air and a convective treatment device that receives the stream of pressurized air, distributes it, and provides it for bathing the body of a person in a general bath of cooled air in order to produce a desired clinical effect such as prevention or alleviation of hyperthermia or for thermal comfort. Such an adaptor may be embodied as an enclosure having a shaped internal cavity. The shape is useful for effectively and efficiently distributing a flow of pressurized over, around and through a bed of ice disposed in the cavity. Ports are provided in the enclosure for introducing a flow of pressurized air into, and receiving a flow of pressurized air from, the cavity.

28 Claims, 13 Drawing Sheets

APPARATUS TO ADAPT A CONVECTIVE TREATMENT SYSTEM OR DEVICE FOR COOLING

FIELD OF THE INVENTION

This invention relates generally to an adaptor for a convective treatment system, and, more particularly, to an ice-actuated apparatus for adapting convective treatment devices and systems to cool a person or animal.

BACKGROUND OF THE INVENTION

The management of body core temperature by convective treatment is known. Convective treatment devices operate by receiving and distributing a flow of pressurized, thermally-conditioned air, and then expelling the distributed air through a surface to provide a generalized bath of thermally-conditioned air over, along, or around a person. To date, the predominant use of convective treatment has been to warm persons. In this mode, a flow of warmed, pressurized air is provided to stabilize or raise the body core temperature of the person in order to amplify comfort or to achieve a clinical objective. One such clinical objective is prevention or alleviation of hypothermia, a condition in which the body core temperature is less than some normal temperature. Convective warming devices have proven themselves to be extremely useful and highly effective in the treatment of hypothermic patients.

There are circumstances under which it would be desirable to deploy a convective thermal device in order to cool rather than warm a person. Again, comfort might be an objective. It might also be desirable to use a convective treatment device to lower the body core temperature. A beneficial effect would be the treatment of hyperthermia, a condition in which the body core temperature is greater than some normal temperature. Hyperthermia may result from environmental heat stress or from illness. Otherwise normal individuals may suffer hyperthermia when their natural cooling mechanisms, such as sweat, are overwhelmed during heavy physical exertion in a hot environment. Heat stress disorders, categorized in ascending order of severity, include heat cramps, heat syncope, heat exhaustion and heat stroke. Normally, a person will voluntarily stop working well before the onset of heat exhaustion, but some persons, such as competitive athletes or military personnel, may push themselves beyond this limit.

Hyperthermia may also be caused by fever associated with illness. Such fevers may have many causes, including infection, tumor necrosis, thyroid storm, malignant hyperthermia or brain tumor. Brain injuries that cause hyperthermia usually involve the hypothalamus, and may be caused by tumors, stroke, head injury or ischemic brain injury due to cardiac arrest.

The physiological consequences of hyperthermia span a spectrum of severity with fluid and electrolyte imbalances, increased cellular metabolic rates, and cognitive impairment being at the low end. In the mid-spectrum, motor skill impairment, loss of consciousness and seizures occur. At the high end, an individual may suffer irreversible cellular injury, especially of the highly metabolic brain and liver cells, and then finally organ failure and death. Hyperthermia is thus a condition that, depending on its severity, may require immediate cooling treatment to return a person's body core temperature to normal.

Cooling treatment may also have other important uses. In some situations, induction of mild-to-moderate hypothermia may provide beneficial protection against injury. The protective benefit of hypothermia has been shown when the blood flow to all or part of the brain is interrupted. Brain ischemia due to an interruption of the blood flow may occur during cardiac arrest, surgery on the brain or open-heart surgery. Cooling the brain before or in some cases after these events occur seems to be protective, and can decrease the severity of the ultimate brain damage.

Because of their eager acceptance and wide deployment, it would be very beneficial and effective to be able to adapt convective thermal devices designed and deployed for warming to also be useful for cooling as the need arises.

In fact, there have been proposals for adapting convective treatment devices to perform cooling. Some involve compounding convective treatment instruments with evaporative mechanisms. In such designs, convection is provided in order to magnify the cooling effects of evaporation. See, for example, the following patents, all owned by the Assignee of this application: U.S. Pat. No. 6,402,775, "High Efficiency Cooling Pads, Mattresses, and Sleeves"; U.S. Pat. No. 6,354,099, "Cooling Devices with High Efficiency Cooling Features"; and U.S. Pat. No. 5,860,292, "Inflatable Thermal Blanket for Convectively Cooling a Body".

One drawback of these adaptations is the need to deal with moisture applied to a body, which may violate certain clinical protocols. In other proposals, air is cooled by the same mechanism that warms and pressurizes it for delivery to a convective treatment device. These mechanisms are, in effect, reversible cycle heat pumps that may be operated to deliver pressurized air that may be heated or cooled, or delivered at an ambient temperature. However, such devices are expensive and require frequent maintenance.

Therefore, there is a need for a simple, inexpensive mechanism that can adapt a convective treatment device to convectively cool a person for enhancement of comfort or for clinical purposes. Preferably, the adaptive mechanism should not require the application of moisture to the person and should not increase the complexity and expense of convective treatment instruments and systems. What is required is an inexpensive adaptor that can be easily and conveniently used to enable a convective treatment device to cool a person rapidly and effectively. Such a device will expand and enhance the utility of convective treatment equipment already deployed for use in warming.

SUMMARY OF INVENTION

It is an object of the invention to adapt convective treatment devices and convective treatment systems for convective cooling. It is also an object of the invention to provide convenient, inexpensive and effective convective cooling of a body (human or animal) by a convective treatment device using an adaptor having a shaped cavity for positioning ice in a stream of pressurized air being provided to a convective treatment device.

The invention solves the problem of adapting existing convective treatment technology already deployed for heat therapy to also provide effective cooling therapy as the need arises.

For convectively cooling a person, a convective treatment system includes a blower assembly, a convective treatment device, and an air hose for providing pressurized air from the blower assembly to the convective treatment device. An adaptor according to this invention may be coupled into the air hose between the blower assembly and the convective thermal device to receive pressurized air, distribute it through a mass of ice for cooling, and redirect it back into the air hose for delivery to the convective thermal device. The convective thermal device has at least one surface with a plurality of apertures that allow thermally conditioned air to flow out of the convective thermal device and bathe a person in air cooled by the ice. In use, the blower assembly provides a stream of pressurized air to the adaptor, where the air is cooled as it flows over, around and through the ice in the shaped cavity. The cooled air is directed out of the adaptor to the convective treatment device whence it is expelled through the apertures, bathing the person in cool air.

The adaptor includes an enclosure with an internal cavity and at least two ports in fluid communication with the internal cavity. Each port supports a flow of air between the internal cavity and the outside of the enclosure. The internal cavity disposes ice in a stream of air flowing through the cavity, from one to the other of the ports. The size of the enclosure can vary, depending on the amount of cooling needed.

The foregoing, together with other objectives, features and advantages of this invention, will become more apparent when referring to the following specification, claims and the accompanying drawings.

DETAILED DESCRIPTION OF THE EMBODIMENTS

The invention concerns an adaptor, intended to operate as a heat exchanger, that is furnished with ice and coupled to enable a convective treatment device to provide a generalized bath of cooled or chilled air to a person. In this regard, the adaptor has an enclosure with at least two ports for supporting a flow of pressurized air through the enclosure. For convenience, throughout this description one port will be denominated an "inlet port", denoting that the so-named port may receive or couple a flow of pressurized air into the enclosure, and the other port will be denominated as an "outlet port", denoting that the so-named port may receive or couple a flow of pressurized air out of the enclosure. The use of the terms "inlet port" and "outlet port" in this description, and in the claims of this application should not be taken to limit the adaptor to supporting a unidirectional flow of air; nor should such use be taken to limit the function of any port to supporting flow of air in only one direction. In fact, the flow of air through the adaptor may, in some designs, be reversible, so that what is in one instance an "inlet port" may well become an "outlet port" in another instance, and vice versa. The adaptor has a cavity, internal to the enclosure, and in communication with a first port and a second port to enable a flow or stream of pressurized air therebetween. The cavity has a shape to position ice in the flow or stream of pressurized air. An example of a convective treatment device with which the adaptor may be used is described in U.S. Pat. No. 5,324,320. A representative convective treatment system may include components marketed under the brand name BAIR HUGGER® by Augustine Medical, Inc., Eden Prairie, Minn., the assignee of this patent application. While the present invention will be described for cooling a person, it could also be incorporated into systems used for cooling other things, such as an animal, a container or a room.

Some optional features of the adaptor include a resealable container for holding ice, an optimized air flow path through the adaptor for increased cooling of the air, and air bypass for air temperature adjustment.

Figure 1:
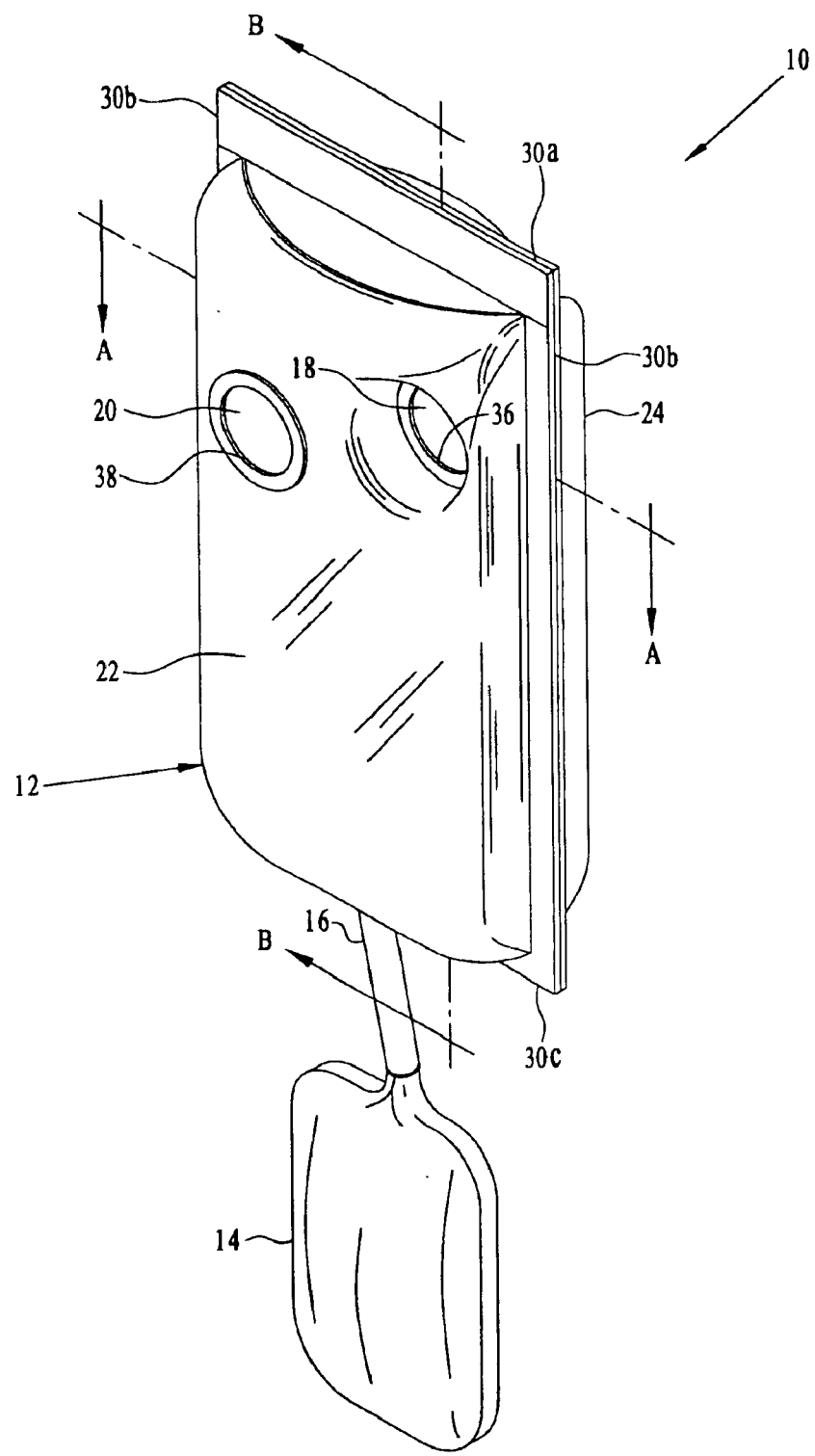
FIG. 1 is an isometric view showing one embodiment of an adaptor according to this invention.

FIG. 1 shows a first embodiment of an adaptor 10. The adaptor 10 comprises an enclosure 12. Optionally, a drain bag 14 may be connected to the enclosure 12 by a drain tube 16. The enclosure 12 has an air inlet 18, an air outlet 20 and may be sized to hold any amount of ice. In the preferred embodiment, the enclosure holds approximately 10 pounds of ice. In the shown embodiment, the enclosure 12 has a front enclosure portion 22 and a rear enclosure portion 24. The front 22 and rear 24 enclosure portions are joined around their periphery 30a (top), 30b (sides), 30c (bottom), forming the enclosure 12 with a cavity 28 (see FIG. 4). The top periphery 30a is designed to allow access to the interior cavity 28 for loading ice in the adaptor 10. The enclosure 12 may be reusable or disposable and may be made of flexible or rigid plastic. In other embodiments, the enclosure may be an integrated, one piece design.

Figure 2:
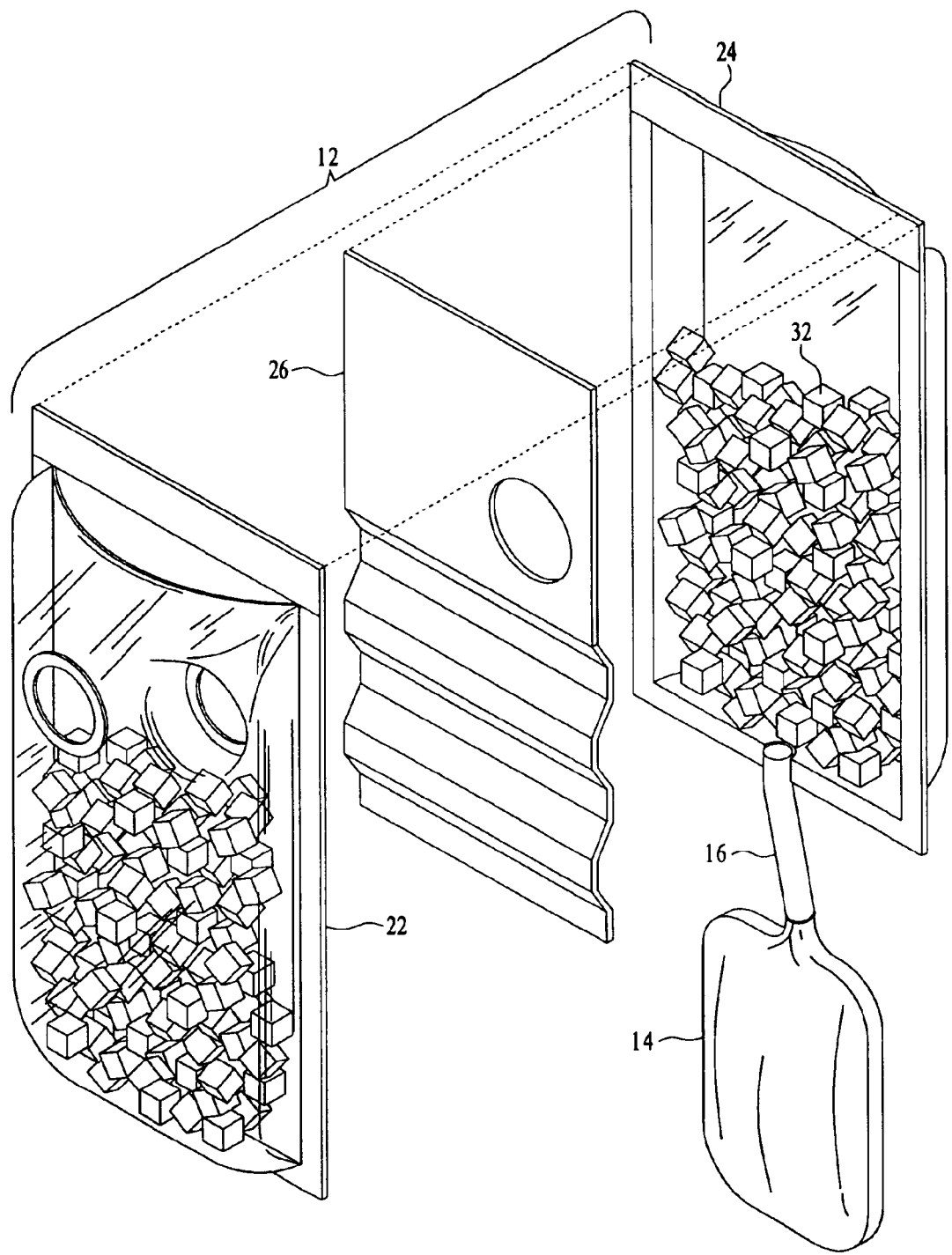
FIG. 2 is a view of the adaptor of FIG. 1.
Figure 3:
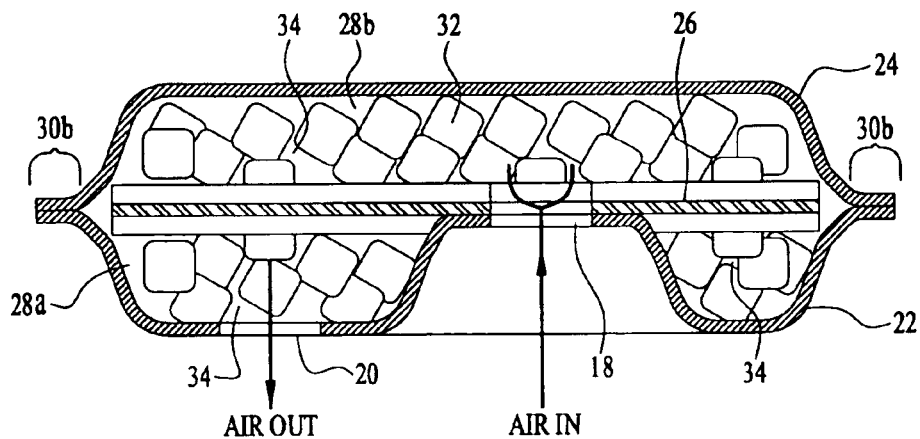
FIG. 3 is a sectional view taken along A—A of FIG. 1.
Figure 4:
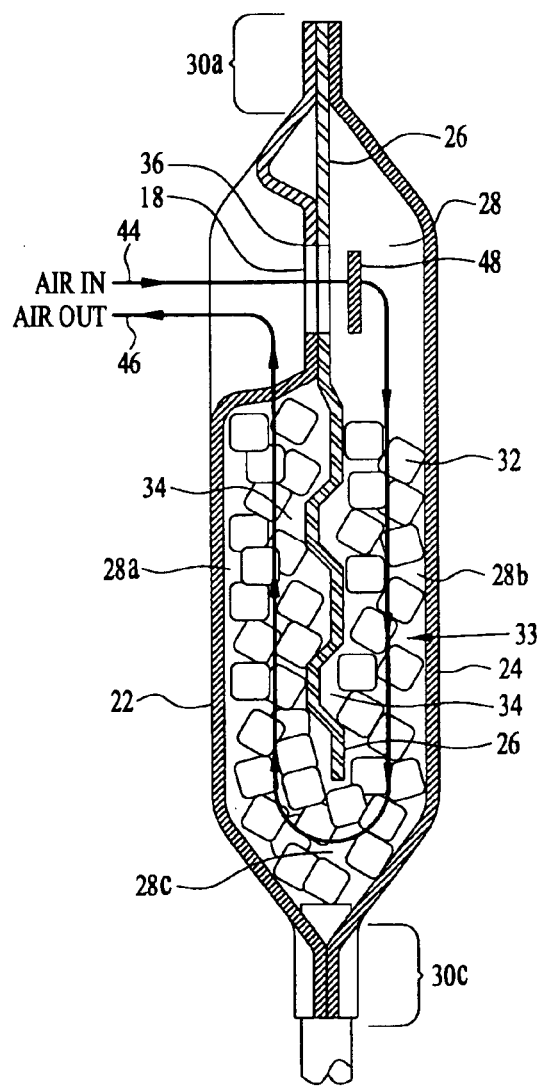
FIG. 4 is an enlarged sectional view taken along B—B of FIG. 1.

Referring now to FIG. 2, a membrane or internal wall 26 is positioned between the front enclosure portion 22 and rear enclosure portion 24. The wall 26 can be constructed of different shapes and materials, which will be described in more detail below. In the preferred embodiment, the wall 26 is a corrugated design. The wall is positioned between the front and rear enclosure portions (22, 24), extending from the top 30a bisecting cavity 28 such that the cavity 28 has a shape. In this example, the shape is a "U" shape, although this is not meant to exclude other equivalent shapes such as the "V" and "C" shapes. The "U" shape is best seen in FIGS. 3 and 4, where the cavity 28 is labeled in 3 sections, a front cavity section 28a, a rear cavity section 28b and a lower cavity section 28c. The front cavity section 28a is formed between the front enclosure portion 22 and the wall 26. The rear cavity section 28b is formed between the rear enclosure portion 24 and the wall 26. The lower cavity section 28c is formed between the front enclosure portion 22 and the rear enclosure portion 24, below the wall 26.

Referring again to FIGS. 3 & 4, a mass of ice portions 32 (which may be cubes, nuggets, flakes, shavings, crushed portions, reusable ice or any equivalents) is received in the cavity 28, the mass 32 forming an ice bed 33. For the adaptor to function properly, air must flow through the ice bed 33 to be cooled. Therefore, the ice bed 33 should be porous. Due to the shape of the mass 32, voids or channels 34 are formed in the ice bed 33 through which air can flow. An optional air diffuser 48, shown in FIG. 4, may be present to reduce the airflow velocity as the air enters the enclosure 12. Pressurized air may enter the adaptor as a jet of 30 cubic feet per minute or more. The air diffuser 48 spreads the air out and reduces the velocity of the airflow. Otherwise, a jet of air may lead to preferential melting where the air hits the ice bed 33. This preferential melting may lead to an unwanted air bypass.

Figure 5:
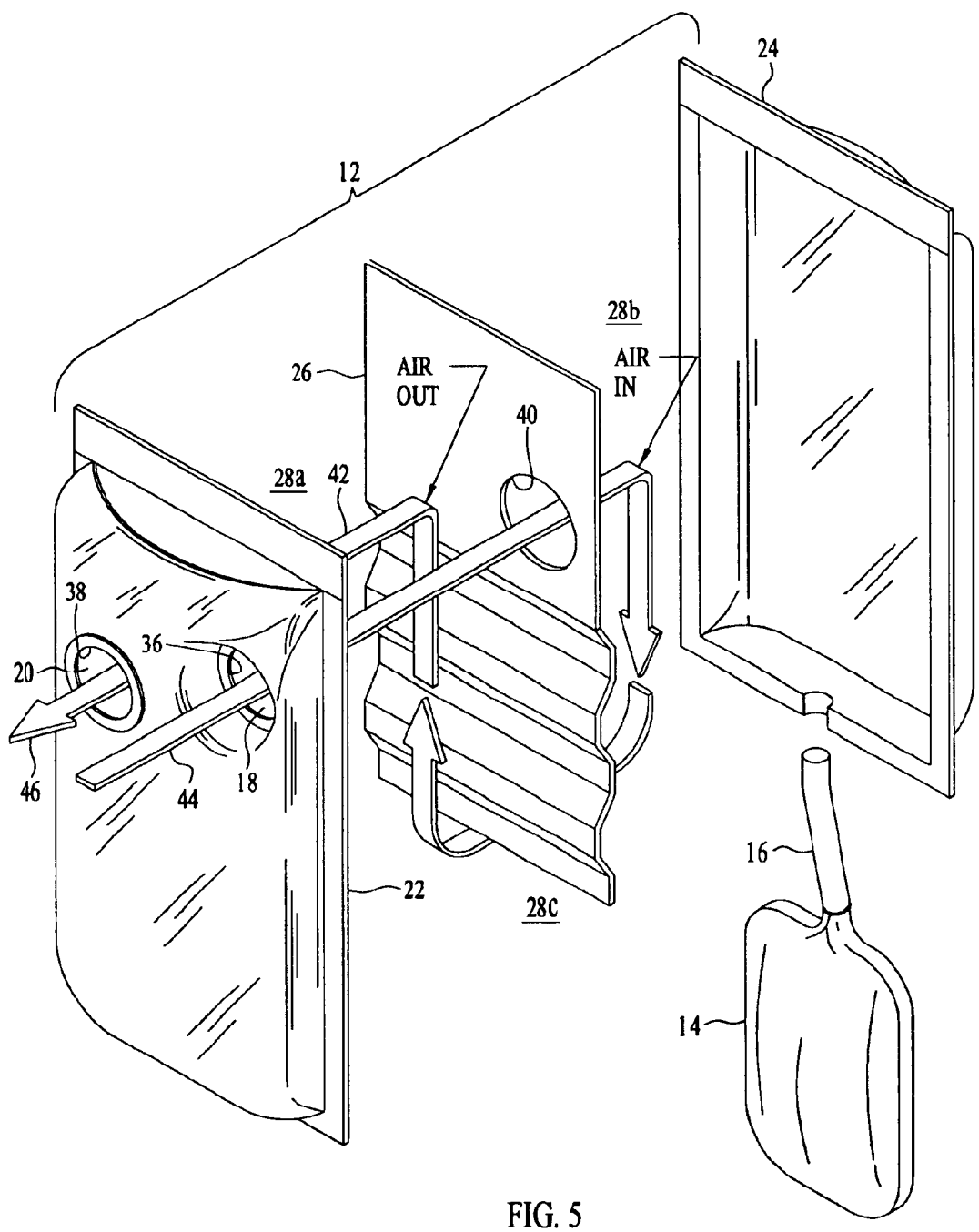
FIG. 5 is another exploded view of the adaptor of FIG. 1 showing the air flow path through a cavity (with ice omitted)

FIG. 5 is an exploded view showing the air path 42 through the adaptor 10. Near the top of the front enclosure portion 22 are two access cutouts, an air inlet cutout 36, corresponding to air inlet 18, and an air outlet cutout 38, corresponding to air outlet 20. The air inlet cutout 36 is attached to a matching wall cutout 40 so that the air inlet 18 accesses the rear cavity portion 28b. The air outlet 20 accesses the front cavity portion 28a through air outlet cutout 38. Pressurized air 44 enters the cavity 28 of the adaptor 10 through the air inlet 18. The air flows through the ice bed 33 in a "U" pattern from the rear cavity portion 28b through the lower cavity portion 28c and the front cavity portion 28a. The air is cooled or chilled as it passes through the voids or channels 34 of the ice bed 33. Cooled air 46 exits the adaptor 10 from the air outlet 20. The pressurized air 44 entering the adaptor 12 can be many different temperatures, preferably ambient temperature.

In use, the mass 32 should fill the enclosure 12 to a point below the air inlet 18 and air outlet 20. The "U" shape of the cavity 28 was chosen so that the air inlet 18 and the air outlet 20 are located near the top of the enclosure 12 to prevent any water from the melting ice from dripping into the air inlet 18 or air outlet 20 (or any hoses that may be attached to them). Also with the "U" shape (or equivalent) of the cavity 28, gravity will cause the ice to settle in the base of the enclosure and air will be forced through the ice bed. As the ice melts, water collects or pools at the bottom of the enclosure. Pooling water covers the ice bed and reduces the amount of the mass of ice exposed to the air stream. It may therefore be desirable to drain off the water that collects in the bottom of the enclosure as the ice melts. If so, this can be done by holes in the bottom of the enclosure or the addition of the drain bag 14, suspended under the enclosure 12. As ice 32 melts, the water seeks the bottom of the enclosure 12, flowing into drain bag 14 via the drain tube 16. The water is drained away to keep the ice exposed to the airflow through the ice bed. The drain bag 14 may be removable so that it may be emptied while the cooling therapy continues. In some cases, the drain bag 14 may be omitted and the water may drip out of the drain tube 16 into another type of container, like a bucket, such as a 5 gallon bucket, or drain.

Figure 6:
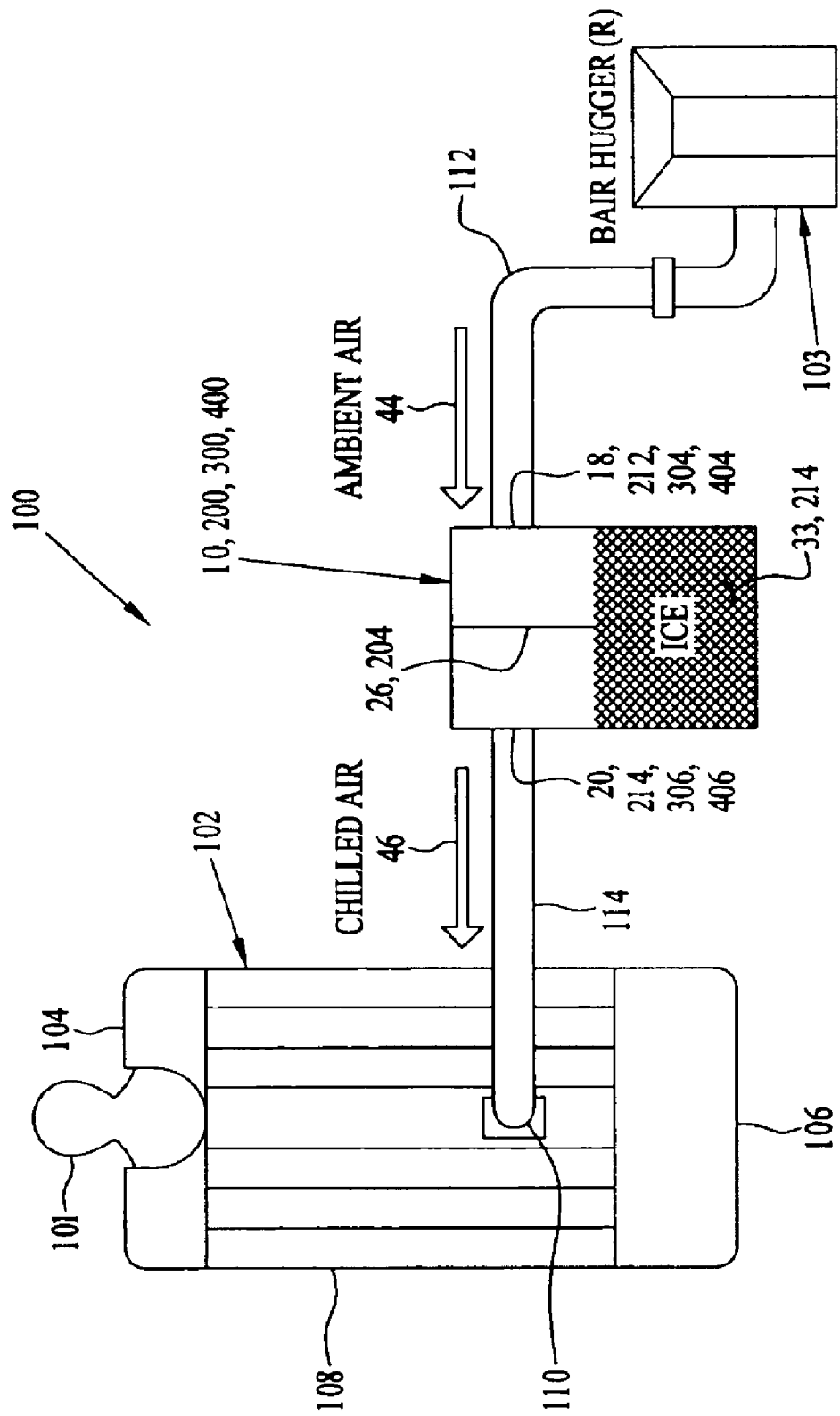
FIG. 6 is a schematic view showing a convective treatment system adapted for use according to this invention for cooling.

FIG. 6 shows one embodiment of a convective treatment system 100 adapted to cool a person 101. The system 100 includes blower 103, an adaptor 10, 200, 300, 400 and a thermal device, such as an inflatable pneumatic blanket 102. The blanket shown here has a head end 104, a foot end 106, lateral edges indicated by 108 and an air inlet cuff 110. On at least one surface of the blanket 102, facing the person 101 to be cooled, are a plurality of apertures (not shown). The shapes, dimensions, pattern and density of the apertures in the blanket may be varied to control the release of the thermally-controlled air to the person. There are many thermal blankets of this type described in the prior art. One such blanket is described, for example, in U.S. Pat. No. 5,324,320. A first air hose 112 is connected between the blower assembly 103 and the air inlet 18, 212, 304, 404 of the adaptor 10, 200, 300, 400. The first hose 112 is provided to carry a stream of pressurized air between the blower assembly 103 and the adaptor 10, 200, 300, 400. A second air hose 114 is connected between the inlet cuff 110 of the thermal blanket 102 and the air outlet 20, 214, 306, 406 of the adaptor 10, 200, 300, 400. The second air hose 114 is provided to carry a stream of pressurized air between the adaptor 10, 200, 300, 400 and the blanket 102.

In use, the blower assembly 103 provides a stream of pressurized air 44 to the adaptor 10, 200, 300, 400 through the first hose 112. The pressurized air then flows through the adaptor 10, 200, 300, 400 and is cooled or chilled by the ice bed, as described with each embodiment. The now cooled pressurized air 46 leaves the adaptor 10, 200, 300, 400 and travels through the second hose 114 into the blanket 102, where the cooled pressurized air 46 is expelled through the apertures, bathing the person 101 in cool air. Tests have shown that a forced-air convective treatment system as described may cool an air stream of roughly 30 cubic feet per minute from room temperature down to 4 to 6° C. for an hour. The cooled air temperature may be maintained for long periods of time without interruption, or continuously if the mass of ice is replenished as it melts.

Ice portions suitable for use with this invention may come in a variety of sizes and may be referred by many different terms, such as cubed, nugget, flaked, shaved or chips. Ice portions with 2 to 3 cm edge dimensions are sometimes termed cubed ice. Smaller, regular shaped ice portions with approximately 1 cm edge dimensions is sometimes termed nugget ice. Irregularly shaped ice portions with the same dimension are sometimes called flaked ice. Even smaller ice portions are sometimes called shaved ice or chips.

Alternatively, the mass of ice may be or include reusable ice cubes, such as sold by Icy Cools, Inc., Kingston, N.J. The reusable ice cubes have a liquid, such as water, sealed in plastic containers that are frozen. The reusable ice cubes are used in place of regular ice and are advertised to provide cooling longer than, up to 30–50%. Another advantage includes no melting water to deal with, which may eliminate the need for a drain. Moreover, once the reusable ice cubes are used, they can be cleaned, refrozen and reused, which may eliminate the need for a ice making source or machine. In addition, the reusable ice cubes may be constructed in a pattern, such as the Ice Snake or Ice Mat sold by Icy Cools, Inc., to allow ease of placement and removal from the adaptor, and to optimize the porosity of the mass of ice.

For cooling purposes, larger cubed ice provides the best mode of operation of this invention because the cubes usually form a more porous ice bed with larger channels or voids. Uniform airflow through a porous mass of cubed ice will produce the most efficient air cooling by melting the ice bed at a uniform rate. Smaller ice sizes pack more densely than cubes, creating smaller voids or channels. The result is that the denser the ice bed, the higher resistance to air flow. Reducing the airflow reduces the capacity of the adaptor for cooling to the patient. Also, the dense ice bed is prone to forming air bypasses as the ice melts. Any non-uniformity in the ice bed, which forms a void, is a preferential path for air. This leads to preferential melting of the ice bed in that area and a preferred channel or air bypass starts to form. This effect may be referred to as "channeling." Once the preferred channel extends through the entire ice bed, air flows through this preferred channel, which then dramatically reduces the cooling effect of the adaptor.

Airflow through larger ice cubes may also form preferred channels as melting occurs, but usually gravity causes the ice to redistribute or collapse and the ice falls into the channels to close them before a complete bypass forms. The ice bed is essentially able to "self-heal" and maintain its uniformity.

As described above, the best performance is obtained when using larger cubed ice because of its ability to form a loose or porous ice bed with many paths for the air to pass through. Nevertheless, in many instances, the only available ice may be the smaller ice, such as nugget, chopped or shaved ice. In such cases, the smaller ice may be placed into a mesh bag, instead of directly into the "U" shaped cavity of the enclosure. The ice filled mesh bag is then deposited in the cavity to form the ice bed. The mesh bag is sized such that when it is deposited in the cavity, air can still flow around mesh bag. The ice bed formed by the mesh bag filled with ice may not have as much surface area exposed to the air as the previously disclosed ice bed and may not cool as efficiently as the large cubed ice bed.

Figure 7:
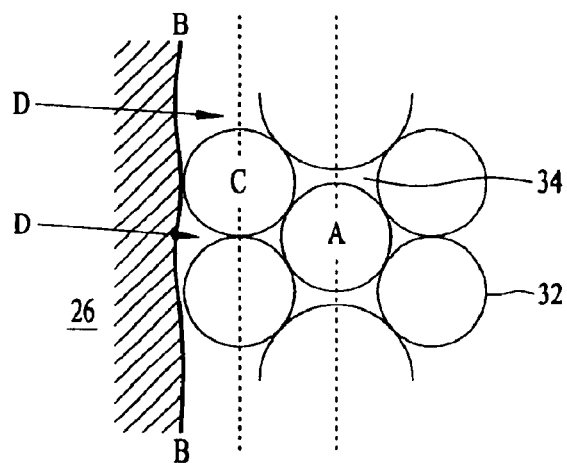
FIG. 7 is an enlarged sectional view showing the relationship between ice and a flat internal wall.

Channeling typically occurs along the wall 26. FIG. 7 shows a visualization of a porous ice bed on a small scale, with the ice 32 shown as a packed array of spheres. With air blowing between the spheres, a discontinuity is formed where the array meets the wall. The porosity or voids between the along planes cut at "A" and "C" are similar, but the interface of the array with the wall "B" creates larger voids labeled "D". Airflow will preferentially follow larger "D" path, leading to faster melting along the wall and eventually formation of a preferential channel.

Figure 8:
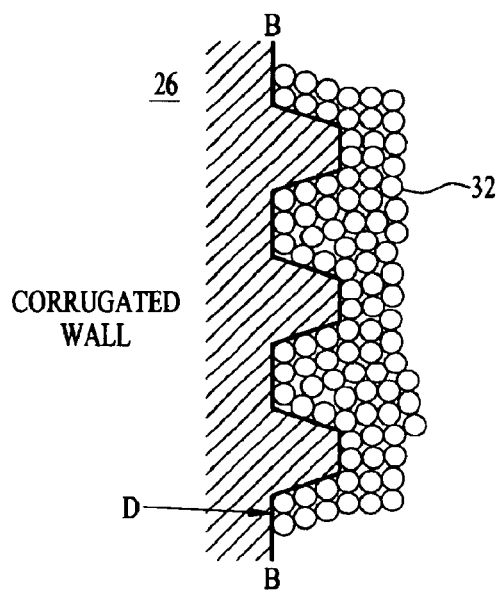
FIG. 8 is an enlarged sectional view showing relationship between ice and a corrugated internal wall.

One may limit, or even prevent channeling along the wall by using a non-planar wall. FIG. 8 shows the corrugated wall 26, described above. The corrugations are of a much larger scale than the portions of ice 32 in the ice bed. The voids "D" along the wall "B" remain, but the air path along the corrugated wall forms a tortuous path with increased resistance to air flow. The air prefers to follow a path of least resistance, which is now a path directly through the ice bed 33, through the voids and channels 34, avoiding the path along the wall 26.

Figure 9:
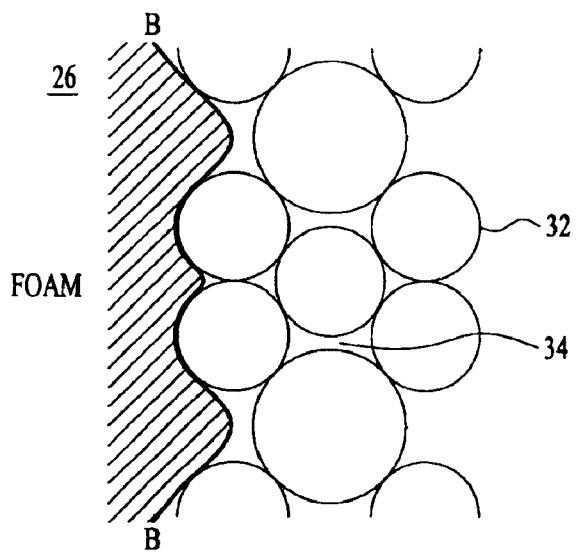
FIG. 9 is an enlarged sectional view showing relationship between ice and a compliant internal wall.

FIG. 9 shows another embodiment for reducing or eliminating channeling along the wall 26. In this configuration the wall 26 is constructed of a compliant material, such as a foam material. This compliant material deforms with the array of ice portions to close the voids "D" at the wall "B". Without the large voids near the wall, the air flow path along the wall has higher resistance than the air flow through the voids or channels 34 at the center of the ice bed 33. Therefore, the air will flow through the center of the ice bed 33.

Figure 10B:
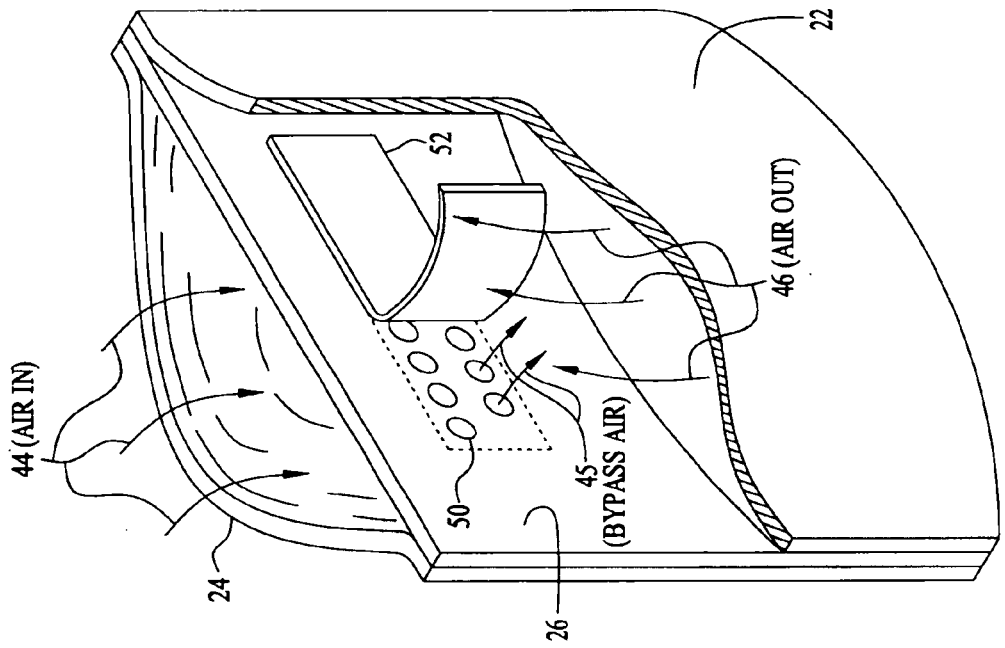
FIGS. 10A, 10B, 11 and 12 are views showing different embodiments for air bypass to control the exit air temperatures of the adaptor.
Figure 10A:
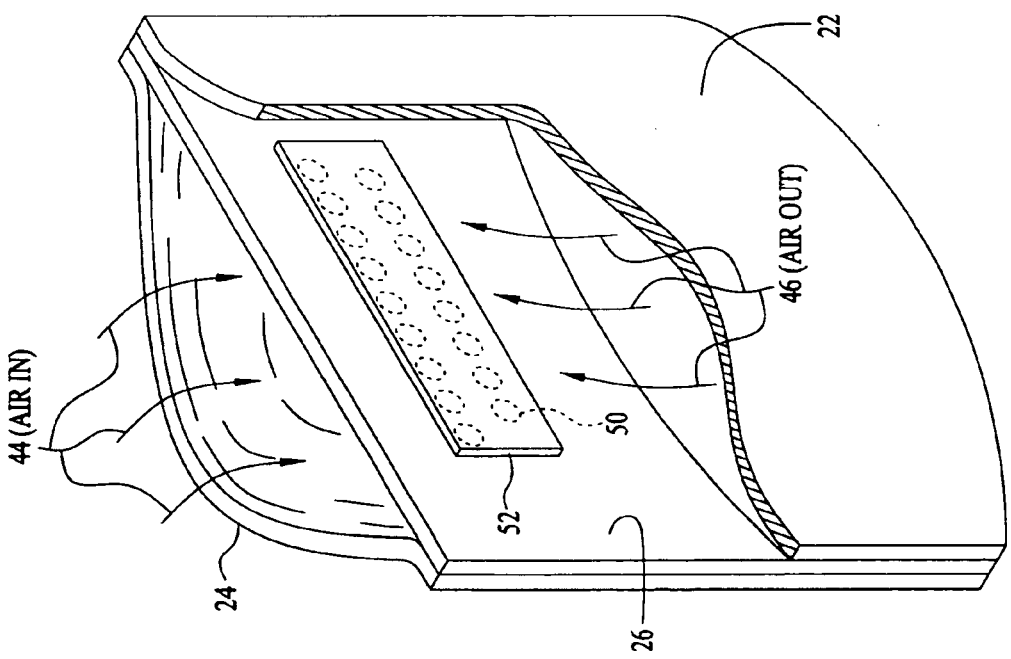
Figure 11:
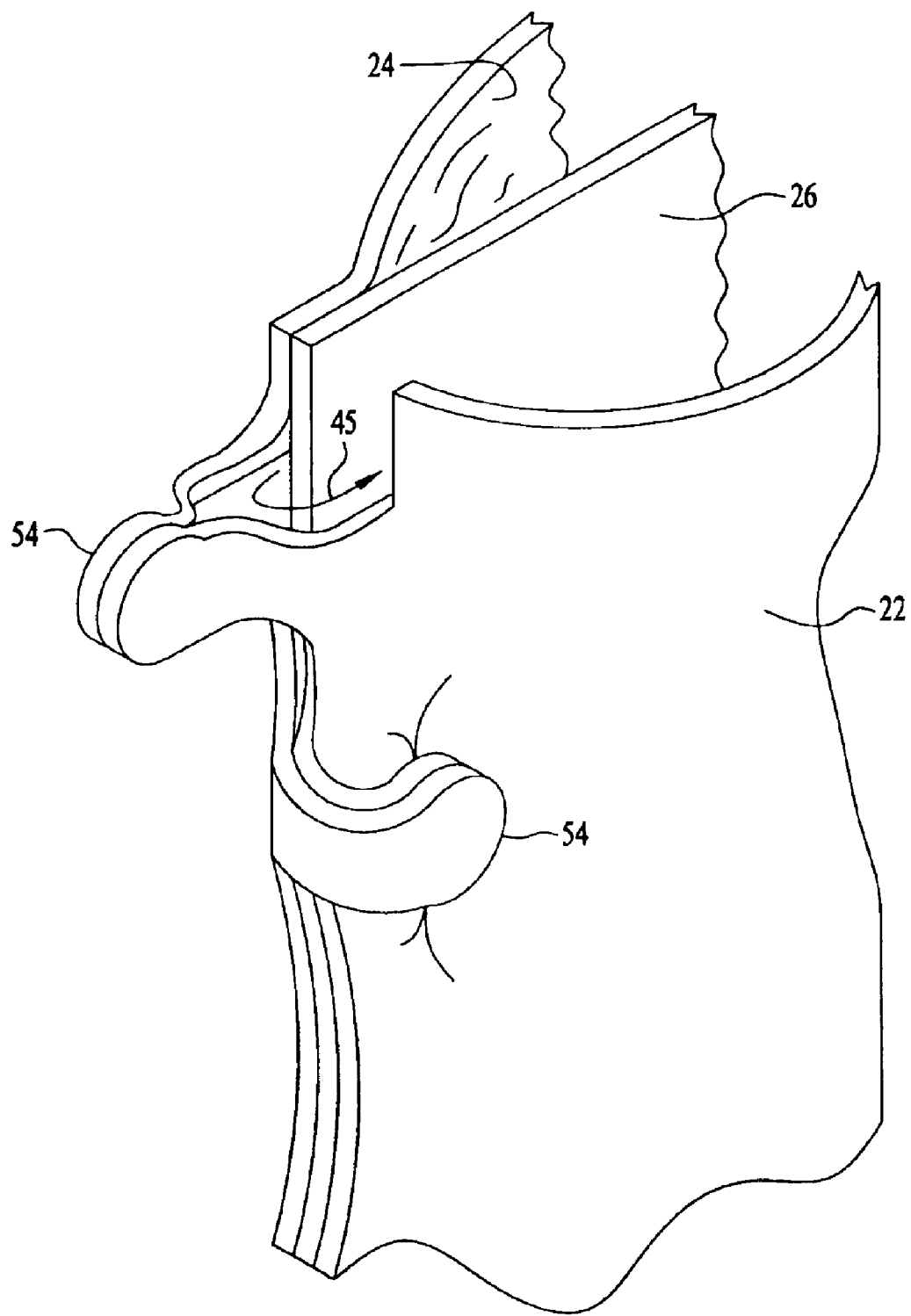
Figure 12:
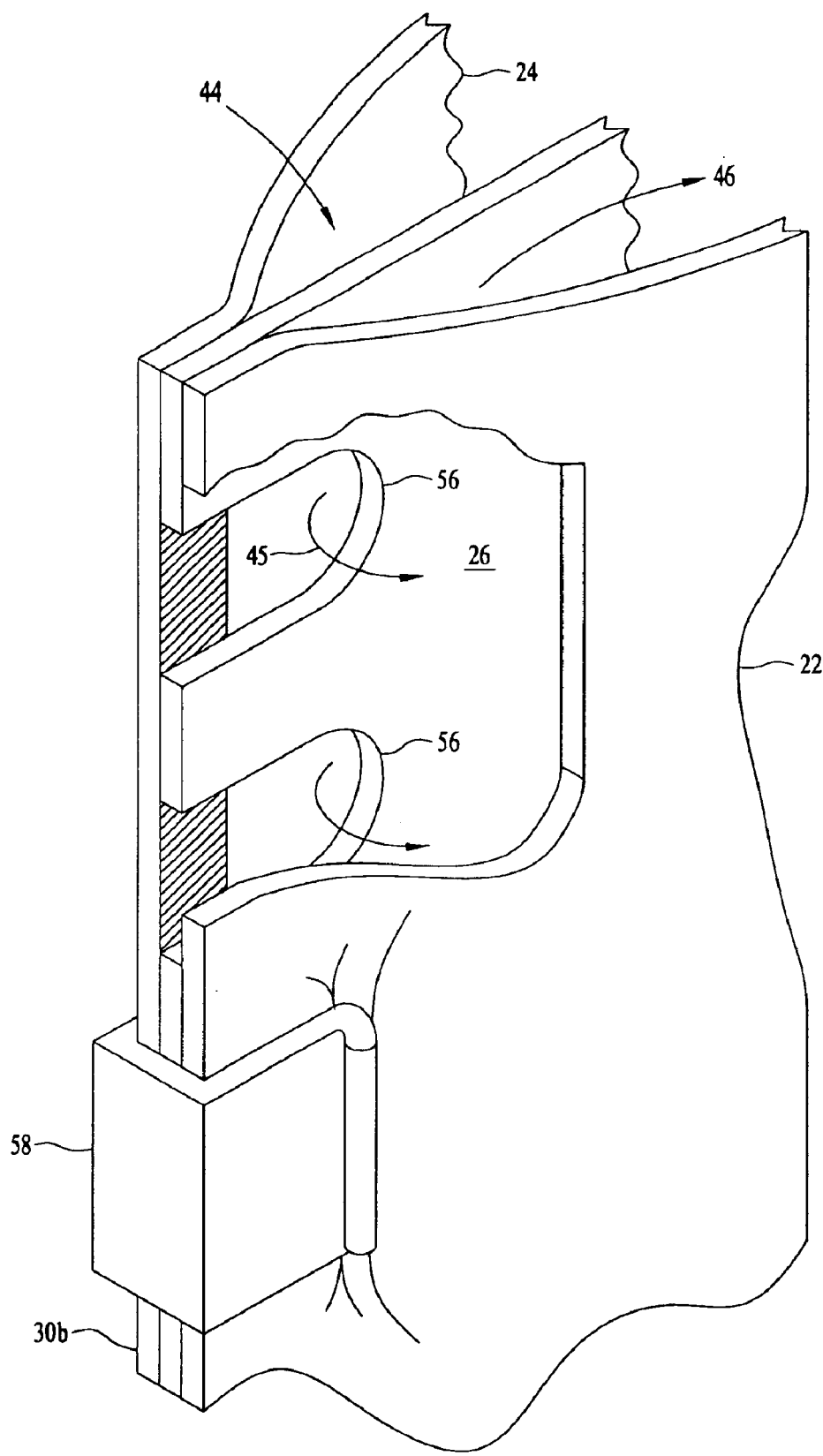

For some applications, provision may be made for adjustably controlling the temperature of the air exiting the adaptor. Such adjustable control may be desired when, for example, a person undergoing convective treatment complains that the air delivered by the forced air cooling system 100 is too cold. In such cases, there needs to be a mechanism for adjusting the temperature of the cooled air produced by the adaptor. This may be accomplished by mixing air which has been cooled by passage through the ice with air at a higher temperature. Such air may be air that enters the adaptor through the inlet port that is not cooled by the ice but is mixed with air cooled by the ice, thereby raising the temperature of the air exiting the adaptor. Adjustable control of the temperature of air exiting the adaptor is achieved by controlling one or more parameters of the uncooled air, including its temperature, its volume, and its velocity. FIGS. 10A, 10B, 11 and 12 illustrate embodiments of mechanisms that adjustably control the temperature of air exiting the adaptor by diverting air at an ambient temperature entering the adaptor through the inlet port. The diverted air circumvents the ice and is mixed with cooled air before or as the cooled air exits the adaptor. Diversion and mixing are supported by provision of a first passage through the cavity in which air flows through ice in the cavity, and a second passage that circumvents the ice. In FIGS. 10A & 10B, the wall 26 is shown having a plurality of bypass holes 50 covered by a removable cover 52. In FIG. 10A, the cover 52 is in place so no air can flow through the bypass holes 50. In FIG. 10B, the cover 52 is partially removed, exposing some of the bypass holes 50 in the wall 26, allowing pressurized air 45 to flow through the uncovered holes 50 and circumvent the ice bed 33. Preferably, the air flowing through the bypass holes is at an ambient temperature. The air 45 then mixes with the air cooled by the ice bed, raising the temperature of the exiting cooled pressurized air 46. The temperature of the cooled pressurized air 46 can be adjustably controlled by controlling any one or more of the volume, velocity, and temperature of the air 45 that is allowed through the bypass holes 50. FIG. 11 shows another embodiment that uses one or more bypass air passage tabs 54 to allow the air 45 to flow around the wall 26. In this case, the upper tab 54 is open allowing the air 45 to flow around the wall 26 while the lower tab 54 is bent over prohibiting the flow of the air 45. The tabs 54 may also be partially open or closed to control the flow of air 45 thereby controlling the cooled air 46 temperature. FIG. 12 shows still another embodiment that uses one or more bypass cutouts 56 in the wall 26. Clips 58 are used to open and close the bypass cutouts 56. With the clip 58 in place, the front 22 and rear 24 enclosures are pinched against the wall 26, closing the bypass cutout 56. When the clip 58 is removed, the front 22 and rear 24 enclosures separate from the wall 26 allowing air 45 to flow through the bypass cutout 56 and mix with the air cooled by the ice bed. Opening and closing the bypass cutouts 56 can adjust the exiting air temperature. To monitor the air temperature exiting the adaptor, a chromatic temperature strip, or other means of air temperature measurement, may be placed near the adaptor air outlet, near the end of the air hose or near the entry to a thermal blanket, to provide feedback to the user on the delivered air temperature.

Figure 13:
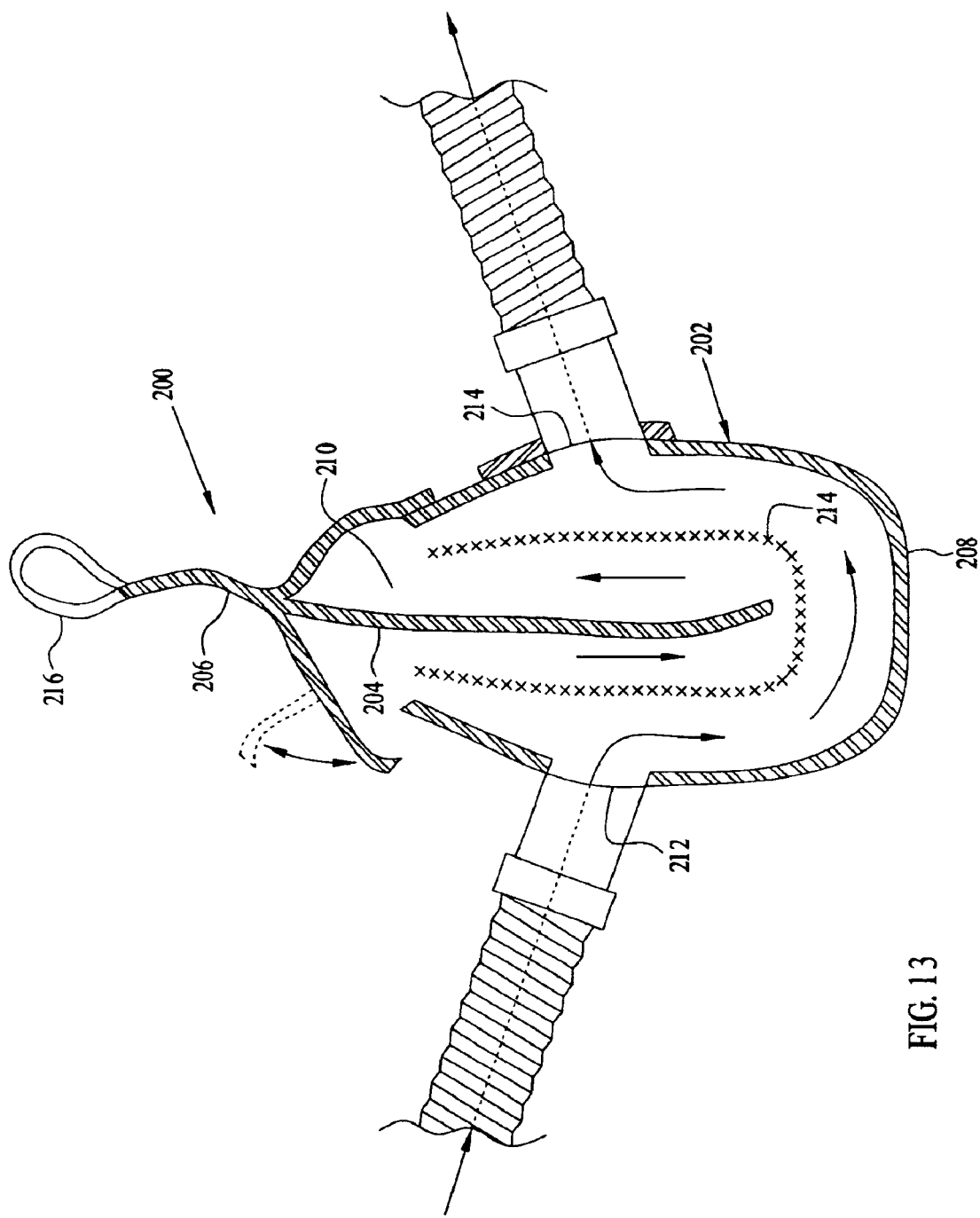
FIG. 13 is a sectional view showing another embodiment of an adaptor according to this invention.

FIG. 13 shows another embodiment of the adaptor 200, comprising an enclosure 202 with an internal membrane 204 joined along a top 206 extending down short of a bottom 208 of the enclosure 202 forming a "U" shaped cavity 210 in the enclosure 202. Opposing ends of the "U" shaped cavity 210 open to an air inlet 212 and an air outlet 214. Ice is placed in the enclosure 202 forming an ice bed 214. A stream of pressurized air flows through, around, over, and past the ice bed. In some cases, the ice bed does not melt uniformly, and the preferred air paths melt faster, forming channels that open to greater and greater airflow. This channeling reduces both the dwell time of air in the ice bed and the amount of surface area of ice that contacts the airflow. One way to attenuate this mode of channeling is to make the enclosure flexible. With this design, the channels collapse from the weight of the surrounding ice over time, due to the flexible enclosure, or they may be collapsed by physically pinching the bag. The delivered air temperature may increase 1° C. due to channeling, and the collapse of those channels may drop the air flow 1° C. The adaptor may also have a handle or structure 216.

Figure 14:
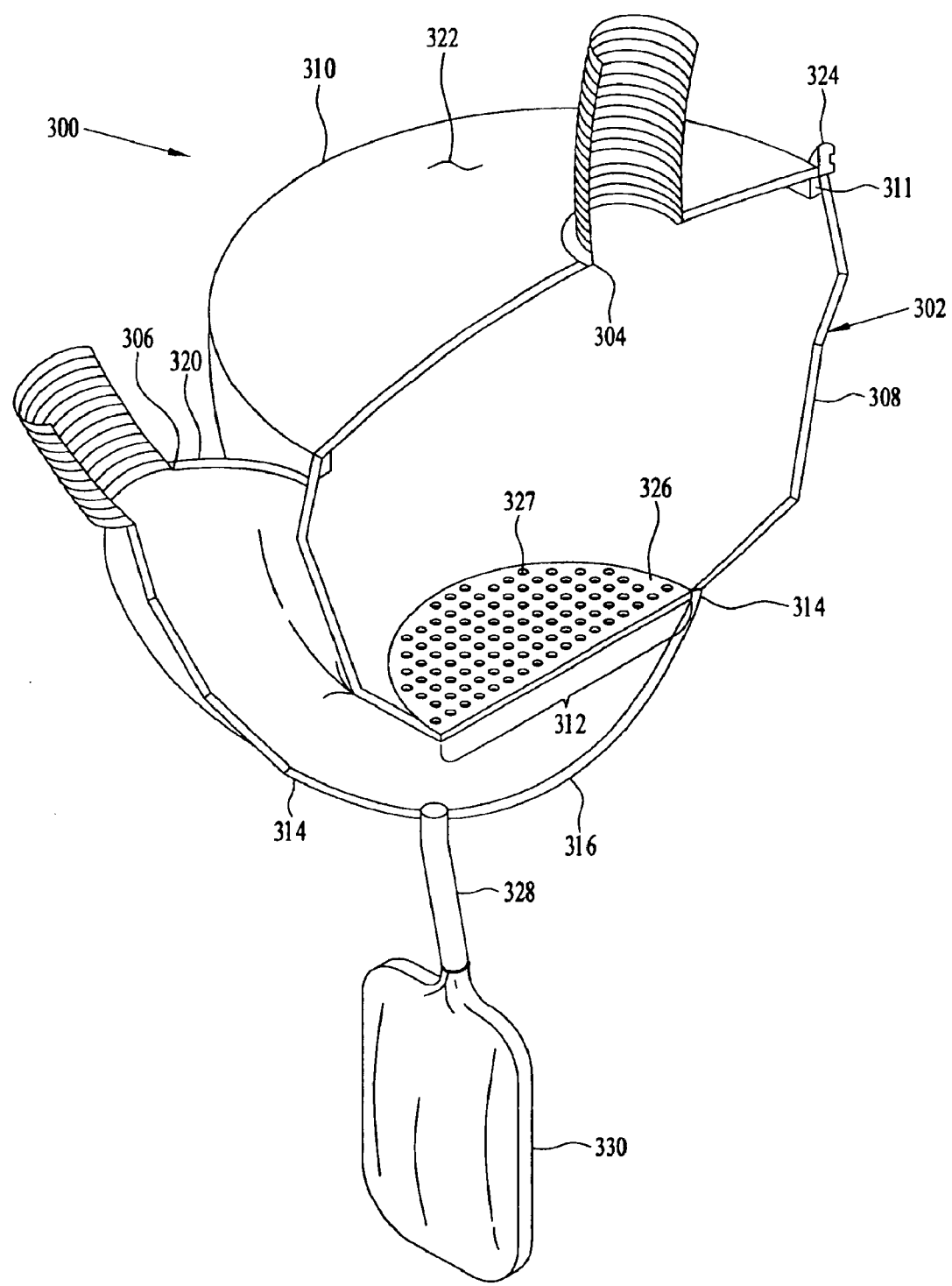
FIG. 14 is an sectional view showing another embodiment of an adaptor according to this invention.

FIG. 14 is a sectional view showing another embodiment of the adaptor 300, comprising an enclosure 302 with an air inlet 304 and an air outlet 306. The enclosure 302 has an internal shaped cavity with a inverted conical or cone-shaped section 308 and a hook or "J" shaped section 314. The conical section 308 has a circular top opening 310 and a lower opening 312 near an apex 313. The top 310 may have a flexible filament 311 that forms the circular shape of the top and stiffens the conical section 308 to keep it open. The air inlet 304 is positioned near the top opening 310. Along a side of the conical section 308, the shaped cavity has a "sealed in hose", that is the hook or "J" shaped section 314, with a lower end 316 in fluid communication with the lower opening 312 and a closed upper end 320 with the air outlet 306. The enclosure 302 also includes an openable top 322 and a clamp or handle 324 to attach the adaptor 300 to an IV pole or other suitable structure. An open mesh 326 is positioned inside the conical section 308 above the opening 312. The mesh 326 supports ice portions (which may be cubes, nuggets, flakes, shavings, crushed portions or any equivalents) that form an ice bed (not shown for clarity but as described in the other embodiments). The mesh 326 has a plurality of openings 327 that allow air to flow through it but are sized to prohibit ice portions from passing through. To insert ice into the enclosure 302, the top 322 is opened and the ice portions are placed inside on the mesh 326, usually below the air inlet 302, forming the ice bed. As the ice melts, water pools or collects at the bottom of the enclosure. The water that collects in the bottom of the enclosure may be drained as the ice melts. This can be done by means of a drain tube 328, which may drain the water into a drain bag 330 or other container, such as a 5 gallon pail, as described with the other embodiments.

Figure 15:
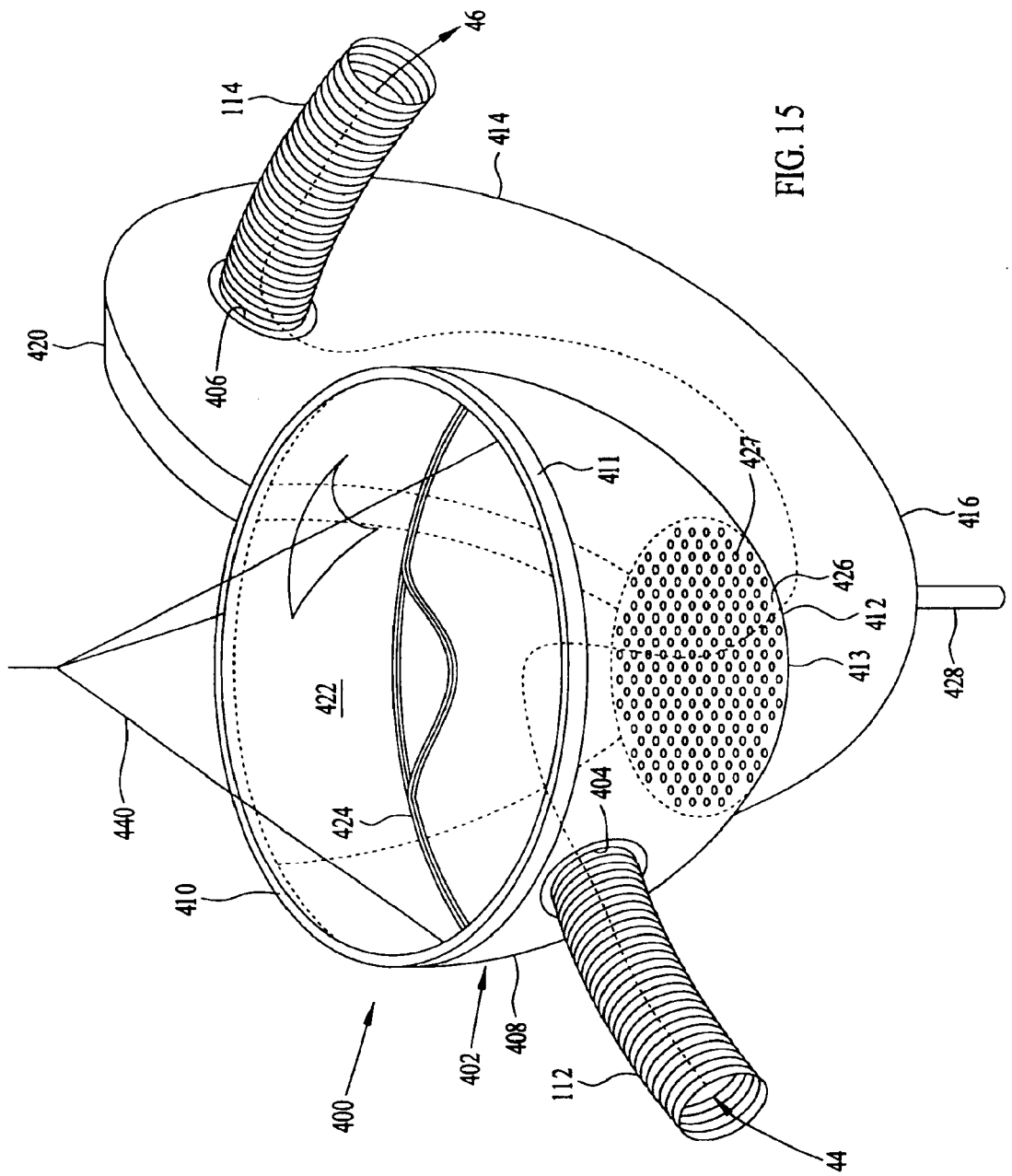
FIG. 15 is an isometric view showing another embodiment of an adaptor according to this invention.

FIG. 15 is an isometric view showing another embodiment of the adaptor 400, comprising an enclosure 402 with an air inlet 404 and an air outlet 406. The enclosure 402 has an internal shaped cavity with a inverted conical or cone-shaped section 408 and a hook or "J" shaped section 414. The conical section 408 has a circular top opening 410 and a lower opening 412 near the apex 413. The top 410 has a flexible filament 411 that forms the circular shape of the top and stiffens the conical section 408 to keep it open. The air inlet 404 is positioned near the top opening 410. Along a side of the conical section 408, the shaped cavity has a "sealed in hose", that is the hook or "I" shaped section 414, with a lower end 416 in fluid communication with the lower opening 412 and a closed upper end 420 with the air outlet 406. The enclosure 402 also includes an openable top 422. In the embodiment shown, the top has a Ziploc® type seal 424 that can be opened and re-sealed. In other embodiments, the top may be completely removable or there may be a flap in the top that is openable and sealable. An open mesh 426 is position inside the conical section 408 near the opening 412. The mesh 426 supports ice portions (which may be cubes, nuggets, flakes, shavings, crushed portions or any equivalents) that form an ice bed (not shown for clarity but as described with the other embodiments). The mesh 426 has a plurality of openings 427 that allow air to flow through but are sized to prohibit ice portions from passing through. To deposit ice into the enclosure 402, the seal 424 is opened and the ice portions are placed inside on the mesh 426, usually below the air inlet 402, forming the ice bed. As the ice melts, water is pools or collects at the bottom of the enclosure. The water that collects in the bottom of the enclosure may be drained as the ice melts. This can be done by means of a drain tube 428, which may drain the water into a drain bag or other container, such as a 5 gallon pail, as described with the other embodiments. The adaptor 400 may be attached to an IV pole, such as described in previous embodiments. In the embodiment shown, hanging elements 440 are attached around the opening 410. The hanging elements can be attached to section 408, the flexible filament 411 or both. The hanging elements 440 are attachable to an IV pole, or other suitable structure capable of hanging, such as a hanger in the ceiling or structure over a bed.

Figure 16:
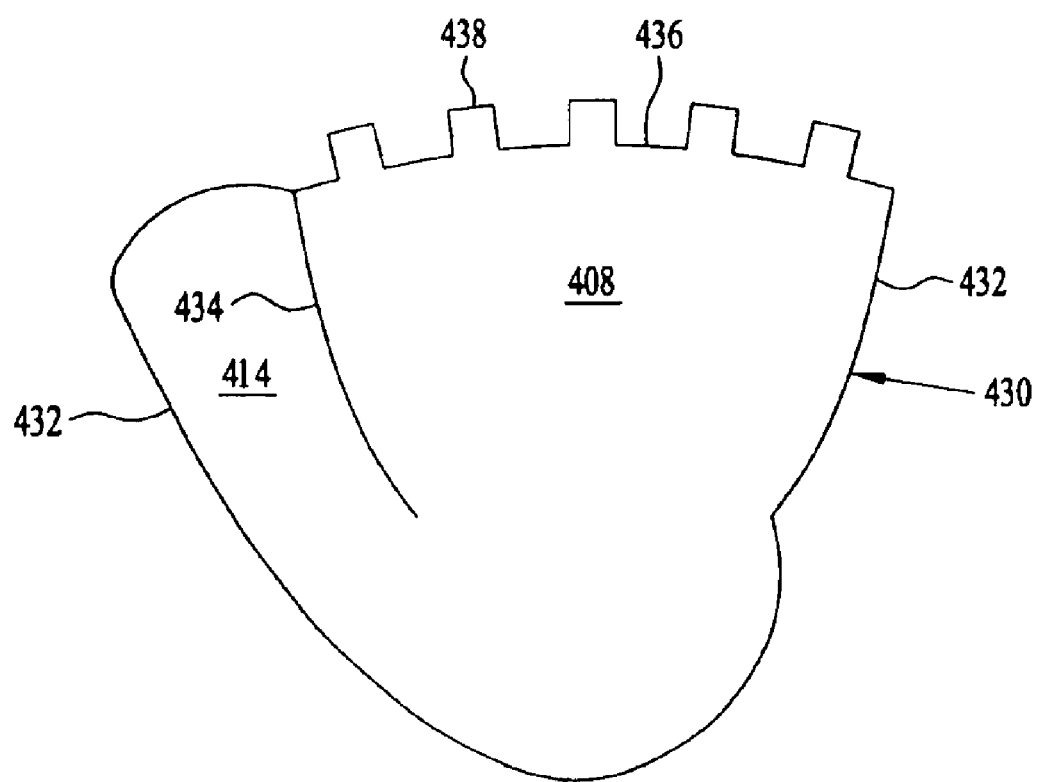
FIG. 16 is a view showing a pattern for an adaptor.

One method of manufacturing the adaptor 400 is now described. The conical section 408 and conduit section 414 may be made using patterns of film, similar to the pattern 430 shown in FIG. 16. The patterns of film can be made out of a plastic material, such as vinyl, between 4 to 12 millimeters thick. The patterns 430 are joined around lower edges 432 and along an internal seam 434. Along a top edge 436 are a number of tabs 438. These tabs 438 are folded over the flexible filament 411 that forms the circular shape at the top opening 410. Once folded, the tabs 438 can be heat sealed in place, making belt-loop type openings for the filament 411 to go through. The flexible filament 411, also referred to as a rigid rim, may be constructed from a flexible plastic, such as PVC. In one embodiment, a piece of PVC, approximately 48 inches long, ½ inch wide and 0.086 inch thick is flexed into a circular shape and joined at the ends. The hanging elements 440 may be made of plurality of cotton strings attached to the flexible filament 411. Three hanging elements 440 are shown in FIG. 15. The mesh 426 may be formed from a hard plastic, such as acrylic. In one embodiment, the mesh 426 is formed in the shape of a bowl with a plurality of ¼ inch holes forming the openings 427. One of the advantages of the bowl shape is that as the ice melts, it keeps collapsing upon itself, "self-healing". Another advantage is that water from the melting ice drains out of the middle of the bowl, at its lowest point, instead of along the sides, which lessens the chance of water being blown up the conduit 414 and into the hose 114. The mesh 426 is inserted into the top opening 410 and attached in place, for example with tape. The air inlet 404 is formed in the conical section 408 and the air outlet 406 is formed in the conduit section 414. A cover 422 is used to seal the top opening 410. The cover should be capable of withstanding the pressure of the air as it enters the conical section 408 and hits the cover 422 from the air inlet 404, the cover 422 acting as a diffuser. One of the advantages in this type of construction is that the only relatively rigid member is the flexible filament 411, therefore, the entire adaptor 400 may be collapsed and positioned inside the flexible filament 411 perimeter, forming a disk shape for easy storage or shipping.

In a method illustrated in FIG. 6, a blower assembly 103 is deployed to provide a stream of pressurized air 44 to the adaptor 10, 200, 300, 400 through a first air hose 112. The pressurized air will enter the adaptor through air inlet 18, 212, 304, 404. If the air hits the ice directly in one place, it tends to melt the ice unevenly and an air bypass can form, making for unpredictable cooling by the device. One way to avoid this mode of channeling is to aim the air away from the ice as it enters. In the embodiment shown in FIG. 4, the air strikes the air diffuser 48 upon entering the adaptor 10. In the embodiment shown in FIG. 13, the air strikes the center wall 204 after entering the adaptor 200. In the embodiment shown in FIG. 15, the air is aimed toward the cover 422 so that as the air enters, it is deflected by the cover 422 and flows downwardly, going through the nooks, crannies, channels or voids of the ice bed where the air is cooled. In other embodiments, the air inlet may direct the air in other directions and from locations (such as the top in FIG. 14). As the air flows through the ice bed, it is cooled. The now cooled air 46 travels out of the air outlet 20, 214, 306, 406 and into the second hose 114. The cooled air 46 travels through the second hose 114 into the thermal blanket 106, where it is expelled through the apertures, bathing a person 101 in cooled, pressurized air. The temperature of the cooled air may be maintained for long periods of time without interruption, or continuously if ice is added to compensate for the melting ice. If the air is too cool, the temperature may be adjusted, for example, by use of one or more air bypasses, as described with the embodiments.

When used with a convective treatment device, the adaptor provides an effective means to cool a person. Useful convective treatment devices are widely available to clinicians. The adaptor may be disposable, or it may be reusable; it may support a unidirectional flow of air, or it may support a reversible flow of air. The adaptor may be small and easy to store, as many clinicians use cooling only on an infrequent basis. The adaptor may eliminate the need for a large or dedicated refrigeration cooling system. The adaptor may also be used in the field, at marathons, sporting events, or other events in hot climates where heat stroke may occur. The adaptor would be effective in humid environments where mist and evaporative cooling products may not function adequately.

Many modification and variations of the invention will be evident to those skilled in the art. It is understood that such variations may deviate from specific teachings of this description without departing from the essence of the invention.

We claim:

1. A convective treatment system for cooling a person, comprising:
   a blower for providing a stream of pressurized air;
   a convective device;
   a first air hose for coupling to the blower;
   a second air hose for coupling to the convective device;
   an adaptor with ports for coupling to the first air hose and to the second air hose;
   a cavity in the adaptor in fluid communication with the ports, the cavity having a shape for positioning ice in a stream of pressurized air directed through the adaptor from the first air hose to the second air hose; and
   an internal wall bisecting a portion of the cavity such that the shape is a "U" shape.

2. The system of claim 1, further comprising opening means in the adaptor for inserting ice.

3. The system of claim 2, wherein the opening means is resealable.

4. The system of claim 1, further comprising a drain tube in fluid communication with the cavity.

5. The system of claim 1, further comprising means for attaching the adaptor to a support.

6. The system of claim 5, wherein the means for attaching is a clamp.

7. The system of claim 5, wherein the means for attaching is a means for suspending the adaptor from a support.

8. The system of claim 1, wherein the ports are positioned above an ice position in the cavity.

9. The system of claim 1, wherein the internal wall is corrugated.

10. The system of claim 1, wherein the internal wall is made of compliant material.

11. The system of claim 1, wherein the internal wall has one or more air bypass passages.

12. The system of claim 1, wherein the shape includes a cone shaped portion in communication with a first port and a hook shaped portion in communication with the cone shaped portion and with a second port.

13. The system of claim 12 further comprising a mesh positioned in the cone shaped portion to support the ice.

14. The system of claim 13, wherein the mesh is bowl shaped.

15. The system of claim 13, wherein the mesh is positioned between the cone shaped portion and the hook shaped portion.

16. The system of claim 15, wherein the second port is positioned at an end of the hook shaped portion, away from the mesh.

17. The system of claim 12 further comprising a flexible filament in the adaptor near a top edge of the cone shaped portion.

18. The system of claim 17 further comprising means attached to the flexible filament for suspending the adaptor from a support.

19. The system of claim 12, wherein the cone shaped portion includes an openable top.

20. The system of claim 19, wherein the fist port is positioned in the cone shaped portion near the openable top.

21. The system of claim 20 wherein the first port directs the air toward the openable top.

22. The system of claim 19, wherein the first port is positioned in the openable top.

23. The system of claim 12 further including one or more air bypass passages between the cone shaped portion and the hook shaped portion.

24. A method for cooling a person using an adaptor with a convective treatment system for cooling a person, the adaptor including ports and an internal cavity bisected by an internal wall with one or more air bypass passages and in fluid communication with the ports, the internal cavity for positioning ice in a stream of pressurized air flowing between the ports, the method comprising:
   providing a convective device;
   providing a first air hose;
   providing a second air hose coupled to the convective thermal blanket;
   disposing ice in the cavity;
   connecting ports of the adaptor to the first air hose and to the second air hose;
   providing a flow of pressurized air through the first air hose to the adaptor; and
   adjusting the temperature of the flow of air by opening and closing the air bypass passages.

25. The method of claim 24, wherein disposing ice includes unsealing the adaptor to receive the ice.

26. The method of claim 25, wherein disposing ice includes resealing the adaptor when the ice is received.

27. The method of claim 24, further comprising draining fluid from the adaptor.

28. The method of claim 24, further comprising attaching the apparatus to a support.

* * * * *

UNITED STATES PATENT AND TRADEMARK OFFICE
CERTIFICATE OF CORRECTION

| | | |
|---|---|---|
| PATENT NO. | : 7,100,394 B2 | |
| APPLICATION NO. | : 10/261160 | |
| DATED | : September 5, 2006 | |
| INVENTOR(S) | : Mark T. Bieberich et al. | |

It is certified that error appears in the above-identified patent and that said Letters Patent is hereby corrected as shown below:

Title Page
Under the heading Assignee, delete "Arizant HealthCare Inc." and replace it with --Arizant Healthcare Inc.--

Under the heading ABSTRACT, line 13, after the word "pressurized" add the word --air--.

Column 3
Line 52, delete the word "an" and replace it with --a--.

Column 9, line 2
Delete the word "a" and replace it with the word --an--.

Column 9, line 35
Delete the word "a" and replace it with --an--.

Column 9, line 43
Delete the reference to "I" and replace it with a reference to --J--.

Column 9, line 61
Delete the word "is".

Column 12, claim 20, line 25
Delete the word "fist" and replace it with the word --first--.

UNITED STATES PATENT AND TRADEMARK OFFICE
CERTIFICATE OF CORRECTION

PATENT NO.         : 7,100,394 B2
APPLICATION NO. : 10/261160
DATED              : September 5, 2006
INVENTOR(S)        : Mark T. Bieberich et al.

It is certified that error appears in the above-identified patent and that said Letters Patent is hereby corrected as shown below:

Column 12, claim 24, line 44
Delete the words "thermal blanket" and replace them with --thermal device--.

Signed and Sealed this

Eighth Day of July, 2008

JON W. DUDAS
*Director of the United States Patent and Trademark Office*